United States Patent
Gatturna et al.

(10) Patent No.: US 6,962,592 B2
(45) Date of Patent: Nov. 8, 2005

(54) ALLOGRAFT IMPLANT CUTTING MACHINE

(75) Inventors: Roland F. Gatturna, Winthrop, MA (US); Andrew R. Sennett, Hanover, MA (US); Richard Faherty, Watertown, MA (US); Dale E. Whipple, East Taunton, MA (US)

(73) Assignee: Cortek, Inc., Dedham, MA (US)

( * ) Notice: Subject to any disclaimer, the term of this patent is extended or adjusted under 35 U.S.C. 154(b) by 312 days.

(21) Appl. No.: 10/241,233

(22) Filed: Sep. 11, 2002

(65) Prior Publication Data

US 2004/0049198 A1 Mar. 11, 2004

(51) Int. Cl.⁷ .................................................. A61B 17/32
(52) U.S. Cl. .......................................... 606/79; 606/184
(58) Field of Search ........................... 606/79, 84, 82, 606/167, 174, 175, 185, 184; 623/923; 30/282, 287; D24/146, 147; 83/684, 685, 686; 144/196, 197

(56) References Cited

U.S. PATENT DOCUMENTS

| | | | | |
|---|---|---|---|---|
| 242,860 A | * | 6/1881 | Barnes | 606/184 |
| 765,954 A | * | 7/1904 | Bernard | 30/363 |
| 1,491,464 A | * | 4/1924 | Coomer | 83/637 |
| 1,742,224 A | * | 1/1930 | Swartz | 269/87.3 |
| 2,250,434 A | * | 7/1941 | Dugaw | 7/158 |
| 3,683,892 A | * | 8/1972 | Harris | 600/567 |
| 3,696,849 A | * | 10/1972 | Davis | 241/262 |
| 3,701,352 A | * | 10/1972 | Bosworth | 606/184 |
| 3,835,860 A | * | 9/1974 | Garretson | 606/79 |
| 4,005,945 A | * | 2/1977 | Gutman | 408/115 B |
| 4,059,115 A | * | 11/1977 | Jumashev et al. | 606/82 |
| 4,092,005 A | * | 5/1978 | Benroth | 241/168 |
| 4,416,278 A | * | 11/1983 | Miller | 606/174 |
| 4,559,936 A | * | 12/1985 | Hill | 606/79 |
| 5,019,081 A | * | 5/1991 | Watanabe | 606/79 |
| 5,423,825 A | * | 6/1995 | Levine | 606/86 |
| 5,437,675 A | * | 8/1995 | Wilson | 606/80 |
| 5,531,756 A | * | 7/1996 | Larose | 606/184 |
| 5,722,977 A | * | 3/1998 | Wilhelmy | 606/84 |
| 6,132,472 A | * | 10/2000 | Bonutti | 623/23.72 |
| 6,231,577 B1 | * | 5/2001 | Canedy | 606/79 |
| 6,458,144 B1 | * | 10/2002 | Morris et al. | 606/179 |
| 6,503,214 B1 | * | 1/2003 | Talish | 602/9 |
| 6,648,894 B2 | * | 11/2003 | Abdelgany et al. | 606/79 |

* cited by examiner

*Primary Examiner*—Eduardo O. Robert
*Assistant Examiner*—David Cornstock
(74) *Attorney, Agent, or Firm*—Burns & Levinson LLP; Frederick C. Williams; Yan Lan

(57) ABSTRACT

The present invention is an apparatus for cutting allograft bone implants from donor bone. Die sets of standard sizes are installed in a press. Donor bone is then placed in position between the upper and the lower parts of a matched cutting set comprising a hollow cylindrical cutting blade, a mandrel, and a table which establishes a gap around the mandrel which guides the blade. After the bone to be shaped has been properly placed, a shaped cutting blade is driven through the donor bone, producing a precisely shaped allograft implant. The invention provides for rapid change out of blades, rapid cleaning, and easy maintenance.

17 Claims, 5 Drawing Sheets

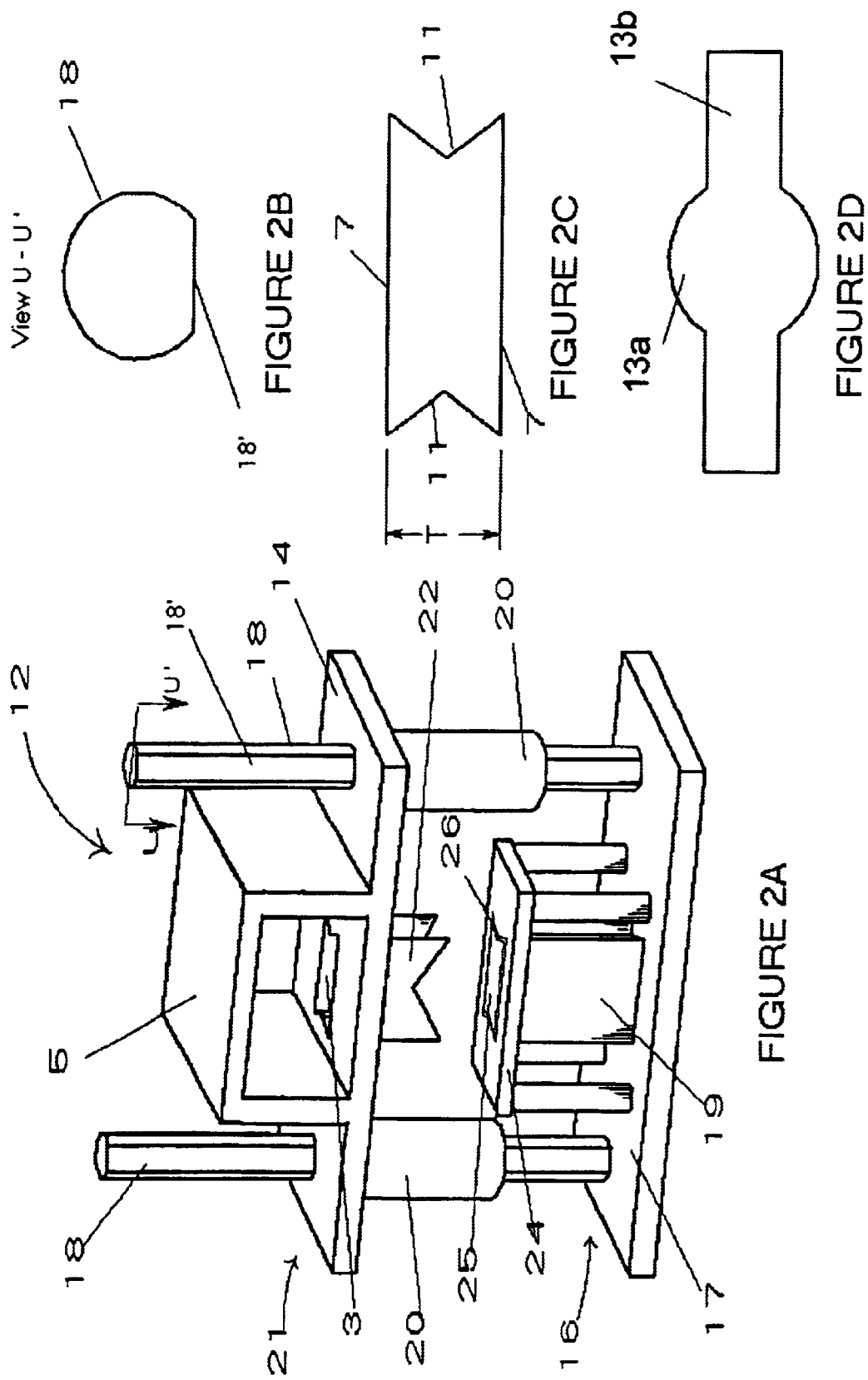

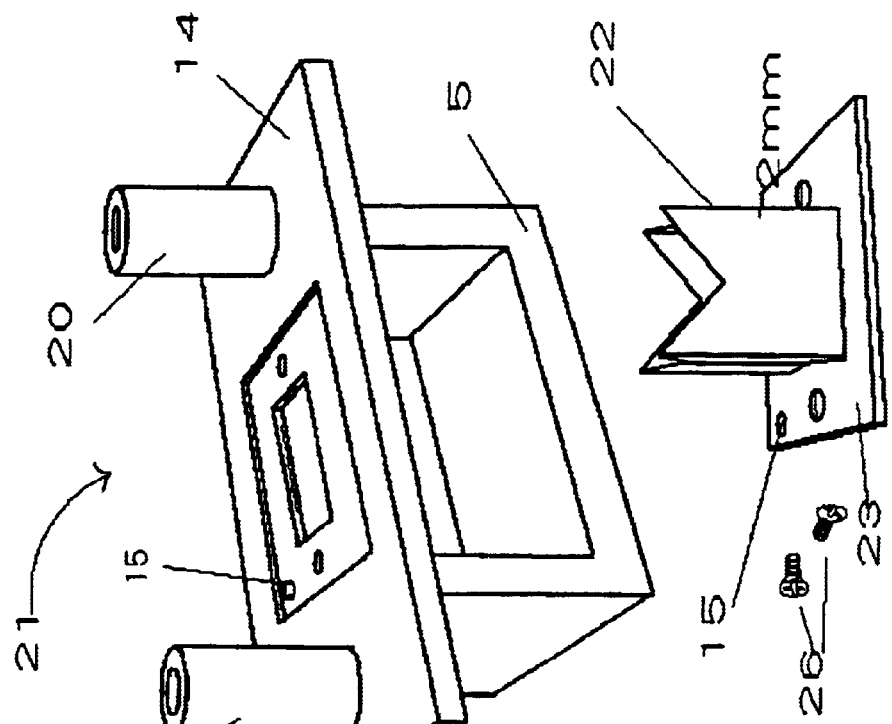
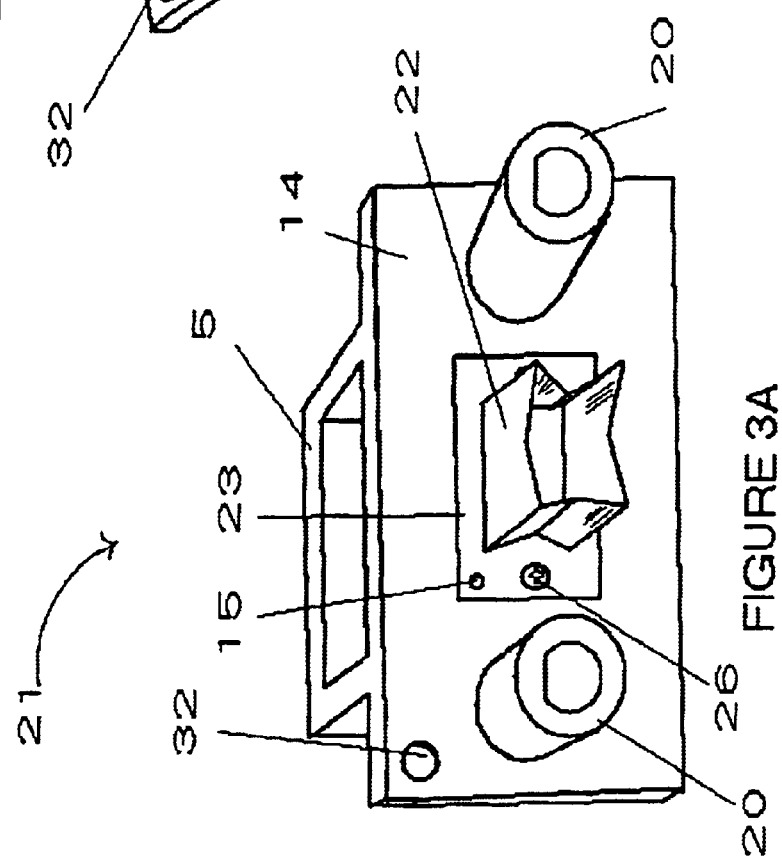
FIGURE 3B
FIGURE 3A

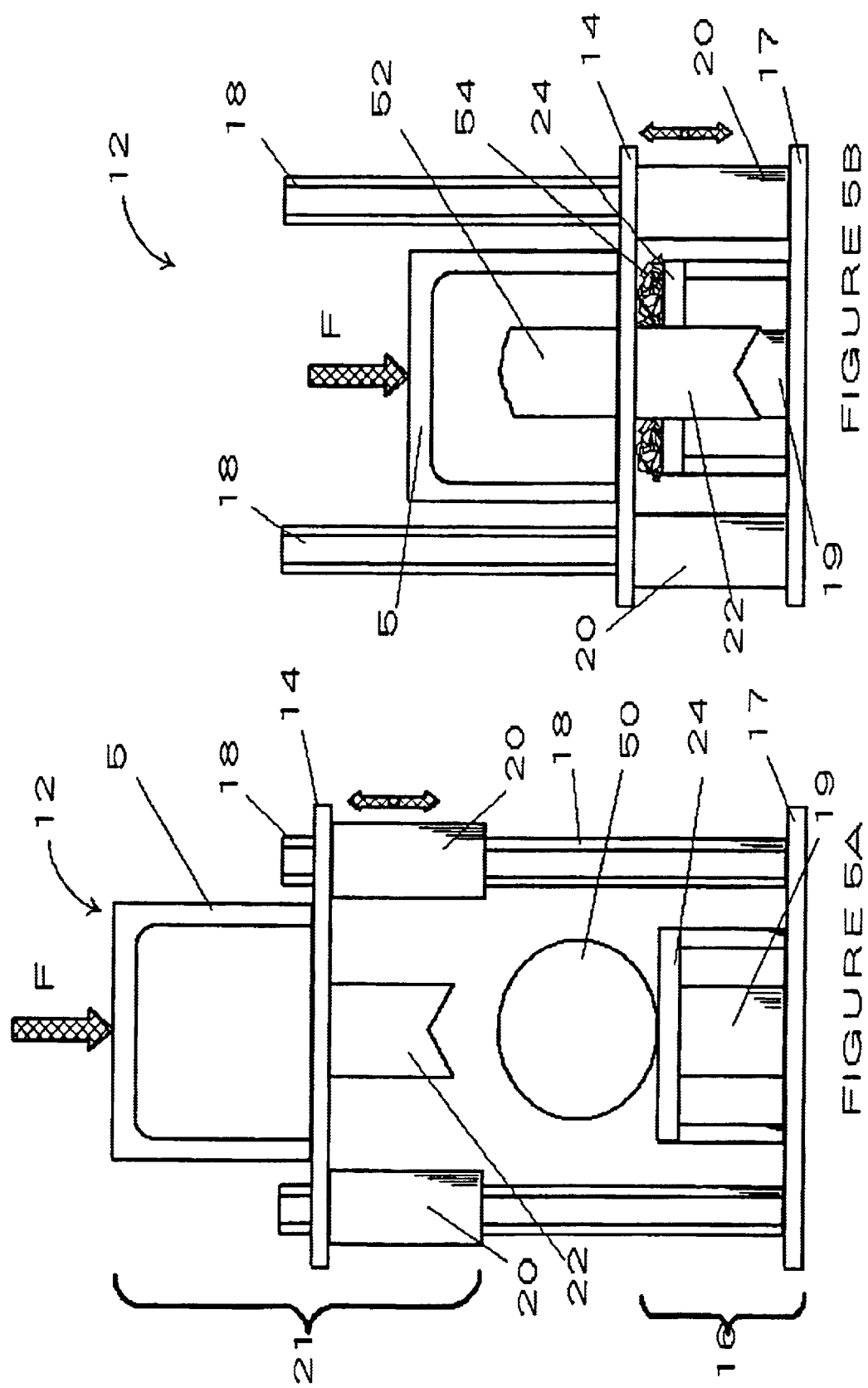

ALLOGRAFT IMPLANT CUTTING MACHINE

FIELD OF THE INVENTION

The present invention relates to implants to be placed into the human body to replace, at least structurally, portions of the body removed because of damage or disease. It also relates to fabricating such implants from tissue donated from deceased persons, commonly referred to as allograft tissue, and in particular it relates to the tools or machines used to fabricate such implants from allograft tissue. It further relates to implants used to replace a portion of the bony structure of the human body, more especially to implants which are designed to fill the intervertebral space created by the partial or complete removal of a damaged spinal disc. Finally and specifically it relates to the apparatus for and method of creating intervertebral implants from allograft bone.

BACKGROUND OF THE INVENTION

Natural intervertebral spinal discs serve, among other things, as cushions and shock absorbers for columnar spinal loadings. In addition, they serve to preserve the spacing of vertebrae necessary for the mechanical integrity of channels which protect the spinal cord and the nerve branches therefrom which innervate various portions of the human body. Frequently, however, accident trauma, degenerative disc disease, and other pathogenesis can compromise all or a portion of the disc's ability to provide mechanical support and integrity.

In such cases, surgical intervention is usually necessary. Surgery sometimes involves only partial laminectomy, but most often the surgeon must remove a portion of the disc so large that replacement of its mechanical, or at least its separative, function is necessary.

In these cases, the most frequent surgical intervention is to attempt to achieve bony fusion of the vertebrae through the space from which tissue has been excised. The process involves inducing fusion of adjacent vertebrae, that is, the joining together of two or more vertebrae by a continuous bridge of new bony tissue. Most frequently an implant serves as a substrate for bone growth.

Many different approaches to fusion have been tried in the last several decades. Examples are metallic and ceramic spacers which are designed to allow the growth of new bone. Prior art devices of this sort have shown very mixed results.

The most promising approach for some time has been the use of human bone as an implant. When this technique succeeds, new bone grows into the implanted bone and provides robust mechanical support between the two compromised vertebrae. Initially it was thought that use of bone from the patient's own body was the best approach. Specially shaped bone transplants from elsewhere in the body, such as from the iliac crest, have been common.

However, use of autograft bone has serious limitations. The use of the patient's own bone to fill the space is less than optimal in that bone obtained from the patient requires an additional surgery site, additional healing and risk of infection, and is available only in relatively small amounts. The latter disadvantage is especially acute when more than one disc must be replaced or when diseased vertebrae themselves must be replaced.

An alternative that readily suggests itself is use of bone from cadavers. Such donor bone, also referred to as allograft bone, is used after preparation that minimizes the likelihood of infection and of immune system rejection by the patient. Cancellous bone is frequently preferred for implantation, because the interstitial spaces allow the ready flow of blood through the implant, which facilitates the growth of new bone tissue. However, cortical bone is also used. The allograft implant must also be prepared by shaping it to conform to the space in which it is to be implanted and wherein it will provide strength and stability to the spinal region from which the damaged or diseased disc has been removed.

Various shapes of bone implants have been used. Roughly circular cylindrical dowels which are inserted horizontally constitute the most common shape in the patent literature but a significant number of other shapes have been tried.

Allograft bone must be shaped into special configurations according to the specific type of fusion graft deemed desirable. For example, the use of a dovetail fusion graft, as disclosed in Nicholson, et al. U.S. Pat. No. 6,096,080, means that an appropriately sized piece of allograft bone must be cut from the donor bone. The most effective use of the tissue donated for specialized bone graft shapes requires that the bone-cutting process must be reasonably efficient and very accurate.

In addition, much allograft bone of interest has specific physical properties which must be taken into account in designing machinery to produce implants from it. In particular, cancellous or trabecular bone has a cellular structure which makes such bone difficult to handle. Allograft bone used for implantation must be treated chemically and physically in order to minimize the risk of transmitting agents of disease or substances which could trigger an immune rejection by the patient. These treatments often include processes as harsh as boiling. As a result, cancellous or trabecular bone in particular, which is frequently of the most interest for spinal implants, is left in an amorphous, soft state which has been characterized as somewhat like a hard boiled egg. Cutting such a substance cleanly and precisely is obviously a challenge. Prior art or obvious methods of shaping such a substance would most likely produce a mushy or crumbled unusable mass.

There is minimal prior art relevant to the tools and machinery for the precision fashioning of allograft implants. In one recently published international application, Shimp and Morris, WO 01/49333 A2, published Jul. 12, 2001, disclose an apparatus for producing bone dowels from allograft long bones. This apparatus relies on the use of a cutter equivalent to a hole saw to core a blank dowel out of, for example, a femur. The principles of operation of that device are very different from those of the present invention. Also, in a series of patents, Bonutti, U.S. Pat. No. 6,132,472, issued Oct. 17, 2000, U.S. Pat. No. 5,888,219, issued Mar. 30, 1999, U.S. Pat. No. 5,662,710, issued Sep. 2, 1997, and U.S. Pat. No. 5,545,222, issued Aug. 13, 1996, disclosed use of a tissue press to compress tissue grafts and composites of tissue for implantation. As these inventions generally relate to maintaining the to-be-grafted tissue in a living condition until implantation, they are generally related to autograft rather than allograft formation. In any event the principles of operation are different from those of the current invention.

Accordingly, one object of the present invention is to provide an apparatus by which to cut allograft spinal fusion implants having standard shapes in multiple sizes from donor bone. A further object of the current invention is to provide an apparatus which can shape bone in a manner consistent with the delicate structure and consistency of cancellous or trabecular bone. Another object of the present invention is to provide an apparatus by which to cut donor bone accurately, with minimum waste, and to provide for easy maintenance, rapid blade changes, and rapid cleanup between batches. Another object of the present invention is to provide an apparatus that provides for an efficient, repeatable means to cut shaped implants in standard shapes and sizes from donor bone. Another object of the present invention is to provide an apparatus that provides a way to cut dovetailed implants in standardized sizes from donor bone. And yet a further object of the present invention is to provide an apparatus by which a single operator can rapidly and safely cut multiple bone implants from a single segment of donor bone.

SUMMARY OF THE INVENTION

For the purposes of this application only, "cylinder" and "cylindrical" are defined to refer to a generalized three-dimensional shape which can be generated by moving a straight line parallel to itself along an arbitrary closed two dimensional curve and perpendicular to the curve. Such a curve can be, but is not limited to, an ellipse, a circle, a rectangle, or a triangle, or some combination thereof.

The present invention is an apparatus for cutting segments of allograft bone into specialized shapes so that they may be implanted in patients. Because of the very particular physical characteristics of purified allograft bone as described above, a central feature of the current invention is to use an apparatus which is analogous to a matched punch and die set with support for the to-be-shaped material both inside and outside the curve along which the cut is to be made.

The support structure of the cutting apparatus comprises a stationary base frame and a horizontal upper plate. The stationary base frame comprises a horizontal base plate, a mandrel, a support portion for the mandrel, a table with an opening surrounding the top of the mandrel, and at least two vertical guide posts. The mandrel sits inside the opening in the table, which is configured so that the opening has the same cross-sectional shape as the mandrel, but is displaced outward by a uniform distance substantially equal to the width of a hollow cylindrical cutting blade, which is described below. The top surface of the mandrel is flat and its top surface and that of the table outboard of the opening are substantially flush.

The horizontal upper plate has a penetration such that the hollow cylindrical cutting blade can be firmly attached to the plate with a substantially vertical orientation and in such a manner that it allows the cut implant portion of allograft bone to slide into the space above the horizontal upper plate, the hollow cylindrical cutting blade being oriented with the cutting surfaces downward. The horizontal upper plate optionally also comprises a force distributing channel arch spanning the penetration. The horizontal upper plate also comprises at least two cylindrical bushings configured to mate slidingly with the at least two vertical guide posts.

Together the arrangement of the hollow cylindrical cutting blade, the mandrel, and the surrounding surface of the table outboard of the opening is analogous to a matched punch and die set. The matched punch and die set analog of this invention comprises the hollow cylindrical cutting blade, which mates slidingly over the mandrel, which has a substantially identical cross sectional shape. It further includes an outer support comprising the cylindrical opening in the table, which is disposed outside the mandrel and shaped such that the cylindrical cross-sectional shape of the opening is substantially the same as that of the mandrel but displaced uniformly outward by substantially the same distance as the thickness of the cylindrical cutting blade and such that the cylindrical cutting blade slides snugly but smoothly into and out of the space established between the mandrel and the opening in the table. In addition, the blade of the hollow cylindrical cutting blade additionally comprises, on the leading, and therefore cutting, edge, protrusions, and in some embodiments points, all with sharpened cutting edges configured so as to slice cleanly into the bone from which the implant is to be cut. The hollow cylindrical cutting blade optionally comprises a flat mounting flange that is detachably secured with machine screws to the horizontal upper plate.

The mandrel located on the stationary base plate slidably receives over it the hollow cylindrical cutter attached to the horizontal upper plate. To operate the apparatus, a segment of bone to be shaped is placed upon the mandrel and on the table and downward pressure is applied to the horizontal upper plate so that the hollow cylindrical cutting blade is driven through the allograft bone blank. The combination of the vertical guide posts and the bushings on the horizontal upper plate function to keep the path traveled by the hollow cylindrical cutting blade substantially parallel to the longitudinal axis of the mandrel, which in the preferred embodiment is vertical. The hollow cylindrical cutting blade, mandrel, and table, collectively referred to as a matched cutting set, may exist in a series of similar sizes defined by at least one size-characterizing dimension.

The flat mounting base flange of the detachable hollow cylindrical cutting blade has an alignment hole that is located to engage a locating pin affixed to the horizontal metal plate to which the flat mounting base flange of the hollow cylindrical cutting blade detachably attaches, and the alignment hole and the locating pin are located according to the size characterizing dimension of a specific matched cutting set. One possible cylindrical cross-section of the matched cutting blade set consists of two parallel opposing flat faces and two opposing dihedral ends designed to cut dovetail shapes. The two opposing dihedral ends are separated by a length, and the size characterizing dimension of the dovetail shape is the width between the flat parallel faces. Dovetail cutters are preferably available in size characterizing dimensions having 1 millimeter increments, and the length dimension is proportional to the size characterizing width for each size characterizing dimension. The size characterizing width is between about 8 millimeters and about 13 millimeters.

The invention also comprises a method of cutting bone implants from donor bone as characterized by using matched cutting sets of a cylindrical cutting blade, a corresponding mandrel and matching table with a central cylindrical cross sectional opening disposed about the mandrel so as to create a slot just the width of the hollow cylindrical blade, upon which a donor bone is placed and the hollow cylindrical cutting blade is forced through the donor bone and over the mandrel.

BRIEF DESCRIPTION OF THE DRAWINGS

FIG. 2A is an oblique view of one of the matched die-set pairs of the present invention;

FIG. 2B is an end-on detail of one of the guide shafts shown in FIG. 2A;

FIG. 2C is a top view of an exemplary cutting blade;

FIG. 2D is a top view of another exemplary cutting blade;

FIG. 3A is an oblique view of the bottom side of the top portion of one of the matched die set pairs, showing the cutting blade;

FIG. 3B is an oblique view of the bottom side of the top portion of one of the matched die-set pairs, with the cutting blade removed;

FIG. 5A shows a die set pair with a vertebral body ready to be cut;

FIG. 5B shows a die set pair with the implant having been cut from the vertebral body.

IDENTIFICATION OF ITEMS IN THE DRAWINGS

Figure 1:
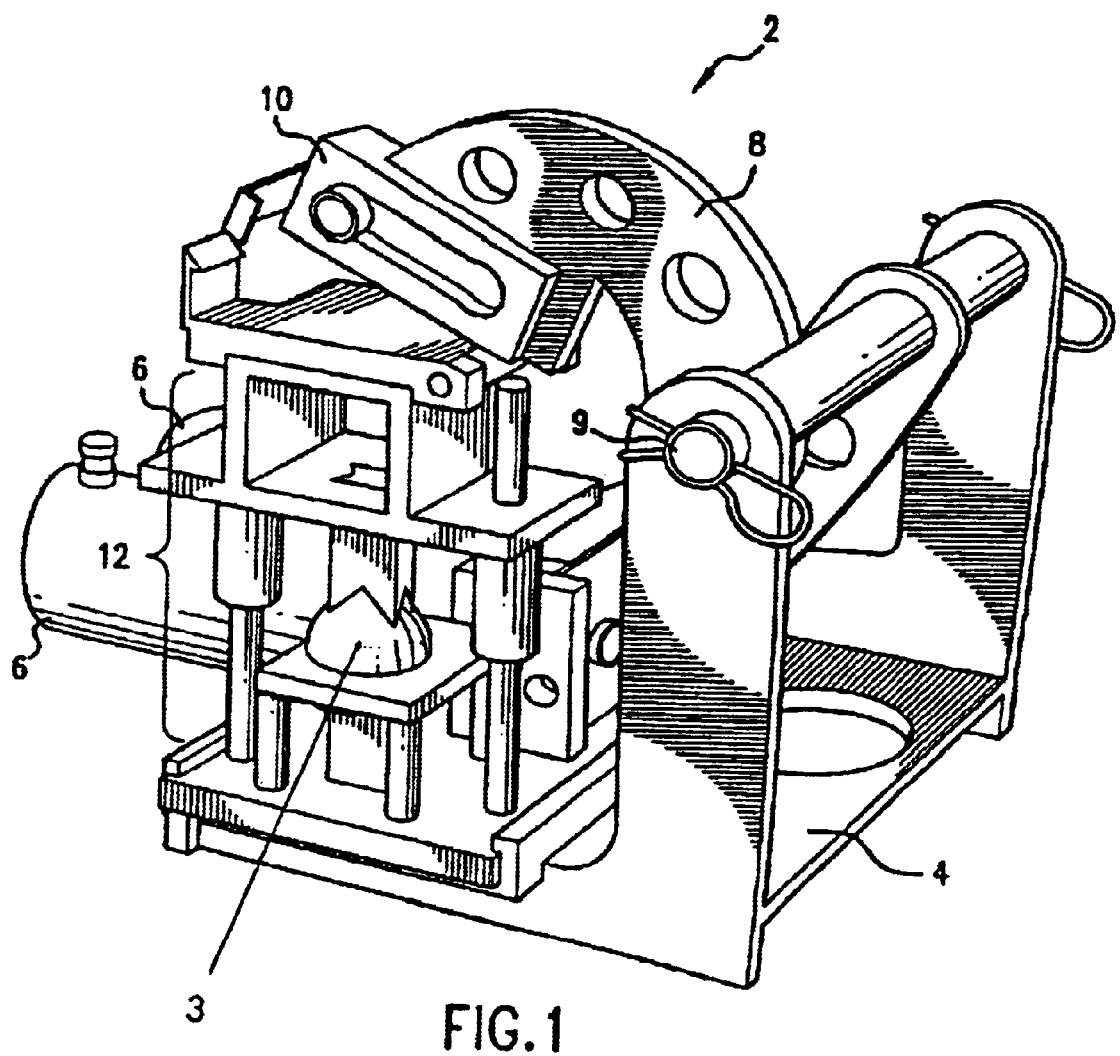
FIG. 1 is an oblique view of the apparatus of the present invention.

FIG. 1
2—vertebral body cutting assembly
3—bone blank
4—base
6—pneumatic pistons
8—swing arm
9—swing-arm shaft
10—transitional sub-assembly which conveys downward force
12—die-set assembly
FIG. 2A
5—force distributing channel arch
12—die-set assembly
14—metal plate part of upper moveable portion or horizontal upper plate
16—lower stationary portion
17—metal plate part of lower stationary portion
18—vertical guide posts
18'—flat surface on guide post
20—bushings
19—vertically oriented support portion of mandrel
21—upper moveable portion
22—hollow cylindrical cutter blade
24—table
25—mandrel
26—clearance gap between 'table' and 'mandrel'
FIG. 2B
18—vertical guide posts
18'—flat surface on guide post
FIG. 2C
7—parallel sides of dovetail
11—dihedral ends of dovetail
FIG. 2D
13a—circular portion of implant shape
13b—rectangular portion of implant shape
FIG. 3A
5—force distributing channel arch
12—die set pair
14—metal plate
15—locator pin hole
20—bushings
21—horizontal upper plate assembly (sometimes referred to as upper moveable portion)
22—hollow cylindrical cutting blade
23—flange of cutting blade
26—flat head alien screws
FIG. 3B
5—force distributing channel arch
12—die set pair
14—metal plate
20—bushings
21—upper moveable portion
22—hollow cylindrical cutting blade
23—flange of blade
26—flat head allen screws
FIGS. 4A through 4D
14—metal plate
15—locator pin hole
15'—locator pin
20—bushings
21—horizontal upper plate assembly (sometimes referred to as upper moveable portion)
22—hollow cylindrical cutting blade
23—flange of blade
26—flat head allen screws
30—location of locator/alignment pin and pin hole
32—key hole(s)
FIG. 5A
5—force distributing channel arch
12—die set assembly
14—metal plate part of horizontal upper plate assembly
16—stationary base frame
17—horizontal base plate
18—vertical guide posts
19—vertical oriented support portion of mandrel
20—bushings
21—upper moveable plate assembly
22—cutting blade
24—table
50—vertebral body
FIG. 5B
5—force distributing channel arch
12—cutting assembly
14—metal plate part of horizontal plate assembly
16—lower stationary portion
17—metal plate part of lower stationary portion
18—vertical guide posts
19—vertically oriented support portion of mandrel
20—bushings
21—upper moveable plate assembly
22—cutting blade
24—table
52—freshly cut implant
54—bone chips

DESCRIPTION OF THE PREFERRED EMBODIMENTS

The present invention is an apparatus for producing bone implants of various shapes and sizes. The production process consists of cutting the implants from human donor bone, also referred to herein as allograft bone.

The apparatus described herein is primarily intended for use in the rapid processing of harvested human donor bones. It provides a precision cut to standard sizes so as to provide the proper fit of the graft during surgical implantation.

The bone cutting apparatus of the present invention consists of a press and a series of cutting die sets in which special hollow cylindrical cutting blades are mounted in a way intended to allow the cutting blade to descend over a matchingly shaped but stationary and vertically oriented mandrel. The mandrel has a substantially flat top held in position by vertical support and is surrounded by a table with a top which has an opening matched in shape to the cross-section of the mandrel but with its perimeter displaced outward by the same amount as the thickness of the hollow cylindrical cutting blade. The table is disposed such that the top surface of the table is flush with the top surface of the mandrel. The mandrel and the table thus together establish a slot into which the hollow cylindrical cutting blade can slide. The table outboard of the slot provides support to the allograft bone blank so that the integrity of the material will not be compromised by the cutting process. The hollow cylindrical cutting blade, the mandrel, and the table comprise a matched cutting set that can cut specific shapes and sizes of bone grafts from allograft bone blanks. The press applies downward force which drives the hollow cylindrical cutting blade downward so as to slice through a piece of bone resting upon the mandrel. The gap or slot between the mandrel and the table controls the sideward or horizontal movement of the blade so that the blade makes a clean cut and the integrity of the blank material is not compromised. The invention also provides safety features such as a unique proximity switch that requires two hands to initiate the bone cutting process and an emergency cut-off switch which can be activated with a single hand.

Each matched cutting set has sharp edges designed for a specific bone slicing or cutting process. The matched cutting set is a shaped cutter of product-specific size and shape designed to precisely cut an implant shape of a specific size, such as a dovetail shape, from a piece of donor bone. In relation specifically to the dovetail shaped implant, the implant is designed to be installed into an intervertebral space which has been prepared such that the dovetail implant locks into the adjacent vertebrae being fused, as described in U.S. Pat. No. 6,096,080.

The matched cutting sets are made in a multiplicity of sizes and shapes. The cutters or die sets are the central feature of the invention; they will repeatedly, and with a single stroke action, produce a precision cut bone graft implant shape. The shape can be any two-dimensional cross-sectional configuration extending the length of the implant being produced, that is, the aforementioned dovetail shape is not the only shape that might be cut with the present invention. The maximum dimension of the implant being cut corresponds, of course, to the size of the donor bone from which the implant is being cut. After the implant is sliced from the donor bone, a final cut-to-length is accomplished with the cut-off tool with the addition of a size-specific test to ensure squareness and precise length control.

The die sets of the present invention are designed for rapid change out in the press to accommodate aseptic batch runs. That is, only the vertebral bodies of a single donor can be in the processing area during the cutting operation. The batch process with the requisite cleaning makes it important to provide for rapid change out of the die sets and for easy cleaning. While one set is being cleaned, another can be moved into place and the process started for another donor's bones. An additional characteristic of this process is the low cost of each die set, as several sets of each die set size are required because after each batch run the die sets must be cleaned and sterilized.

Each given matched cutting set is to be manufactured as a matched set in order not to have one or the other component exchanged with a component of the same size from another set. Also, provisions have been made to ensure that a given size of die cutter blade will be used only with the matching parts with which it was manufactured; the specific provisions are alignment holes and bolt patterns.

Main Parts of the Overall Invention

The operative parts of the apparatus shown in FIG. 1 are the elements of the die set or die cutter assembly 12. Referring now to FIG. 1, there is shown in oblique perspective view the total bone cutting assembly 2 consisting of a base 4, a pneumatic piston assembly 6, a swing arm 8 rotationally attached to the base frame by way of a swing-arm shaft 9. At the distal end of the swing arm 8 is a transitional sub-assembly 10 which conveys downward force from the swing are to a die-set assembly 12 in a way that allows for relative translational motion. A piece of bone blank 3 is shown positioned awaiting cutting. FIGS. 5A and 5B show the basic elements of the bone cutting operation.

The Cutting Assembly

FIG. 2A shows the die cutter or die set assembly 12 in oblique view. The die-set assembly 12 is the central active part of the bone cutting assembly 2 shown in FIG. 1. The die set assembly 12 consists of a stationary base frame portion 16 consisting of a horizontal metal base plate 17, a vertically oriented support portion 19 attached to the stationary base plate and having an uppermost flat surface of a mandrel 25. Surrounding the flat mandrel top surface 25 is a table 24 having a top surface that is flush with the flat mandrel surface; a clearance gap 26 exists between the table and the said uppermost flat mandrel surface 25. The base plate 17 also has attached to it two vertical guideposts 18, each of which has a flat sided surface 18'.

The cutting assembly 12 also has an upper moveable portion, denominated the horizontal upper plate assembly 21, which slides upon the guideposts 18. The upper moveable portion or horizontal upper plate assembly consists of a horizontal metal plate 14 having a penetration 3 through it and two bushings 20 that slide upon the two vertical guideposts 18. The penetration 3 allows the cut portion of allograft bone to slide into the open space above the horizontal upper plate. A hollow cylindrical cutting blade 22 is attached to the horizontal metal plate and oriented downward from beneath the penetration 3 in the horizontal metal plate and able to slide over the vertically oriented cylindrical support portion 19 of the mandrel 25. The hollow cylindrical cutting blade 22 is designed to slide over the mandrel 25 and its vertically oriented cylindrical support portion 19. A rectangular force distributing channel arch 5 spans the penetration 3 and distributes downward force to the moving metal plate 14.

Upon descent of the horizontal upper plate assembly 21, the mandrel 25 of the vertically oriented cylindrical support portion 19 of the stationary base plate 17 can slidably receive over it the hollow cylindrical cutting blade 22 attached to the horizontal upper plate assembly 21. The vertically oriented support portion 19, the mandrel 25, the hollow cylindrical cutting blade 22B, and the table 24 together comprise a matched cutting set. The hollow cylindrical cutting blade 22 mates with the matched mandrel 25 of the male portion 19 which is contiguous with the lower stationary portion 16 of the cutting set assembly 12, and when the upper moveable portion 21 descends, the hollow cylindrical cutting blade 22 descends through the gap 26 between the table 24 and the mandrel 25 at the top of the vertically oriented cylindrical male portion 19, and then the blade 22 descends over the male portion 19. The size and shape of the penetration 3 in the horizontal metal plate 14 of the upper moveable portion 21 is such as to allow passage therethrough of any object that can pass through the internal passageway any given cylindrical shape of the hollow cylindrical cutting blade 22. Together these items comprise a matched cutting set comprising the assembly 12 shown in FIG. 1.

FIG. 2B is a detail of the cross section of the guide posts 18 showing the flat surface 18'. The flat surface 18' ensures that the moving portion 21 gets assembled in the proper orientation to the fixed portion 16.

The cutting blade 22 as shown in FIG. 2A is cylindrical, as defined above. In FIG. 2A the cylindrical shape consists of two opposing and parallel flat faces; FIG. 2C shows the cylindrical shape of the matched cutting blade set consists specifically of two parallel opposing flat faces 7 and two opposing dihedral ends 11 designed to cut dovetail shapes. Other shapes are also contemplated, such as, but not to imply or suggest constraint to only two shapes discussed herein, the one shown in FIG. 2D which is a unitary cylindrical shape having a cross section consisting of a circular portion 13a and a rectangular portion 13b. More specifically, the cylindrical shape of the matched cutting blade set consists of a circle centered upon a rectangle having a length that exceeds the diameter of the circle and a width that is less than the diameter of the circle.

A given matched cutting set shape is characterized in size by at least one size characterizing dimension. For example, in FIG. 2C the dimension T is a size characterizing dimension of the dovetail shape. The cross sectional shapes such as the dovetail shape and the shape consisting of a circle with the rectangle are among possible shapes that can be cut by a correspondingly shaped hollow cylindrical cutting blade and a matched mandrel and table. The matched cutting blade set is of any cross sectional shape considered useful as an implant.

Each hollow cylindrical cutting blade 22, mandrel 19, and table providing a given cut shape constitute a matched cutting blade set having a cylindrical shape defined by one or more size characterizing dimensions such as the dimension T in FIG. 2C. Note that throughout this disclosure, the dovetail shape is the one most commonly referred to in the text and FIGURES, but that the other shape as shown in FIG. 2D in various sizes, as well as additional shapes not shown, are also intended by the inventors to be able to be cut from donor bone by the present invention.

FIG. 3A is an oblique view of the bottom side of the upper moveable portion 21 of the matched die-set pair 12 (FIG. 1) showing the metal plate 14, the bushings 20 and the hollow cylindrical cutting blade 22. FIG. 3B is an oblique view of the upper portion 21 shown inverted with the hollow cylindrical cutting blade 22 shown detached from the plate 14. Machine screws 26 are used to detachably mount the blade 22 to the plate 14 by way of the blade's mounting base flange 23. That is, the cutting blade 22 is detachable from the metal plate 14. Two flat-head allen screws 26 hold the cutting blade 22 in place. The flat mounting base flange 23 of the detachable hollow cylindrical cutting blade 22 has an alignment hole 15 that is located to engage a locating pin 15' affixed to the horizontal metal plate 14 to which the flat mounting base flange of the hollow cylindrical cutting blade detachably attaches. As shown further in FIGS. 4A through 4D, the respective and corresponding location of the alignment hole 15 and the locating pin 15' are located according to at least one size characterizing dimension of a given matched cutting set, such as the thickness dimension T shown in FIG. 2C. That is, the two opposing parallel flat faces and two opposing dihedral ends separated by a length dimension comprise a cutting shape having a size characterizing dimension T that is the width between the flat parallel faces. Specifically in relation to the dovetail implant shape, the size characterizing width T is between about 8 millimeters and about 13 millimeters and most preferably of between about 9 millimeters and about 12 millimeters.

Figure 4A:
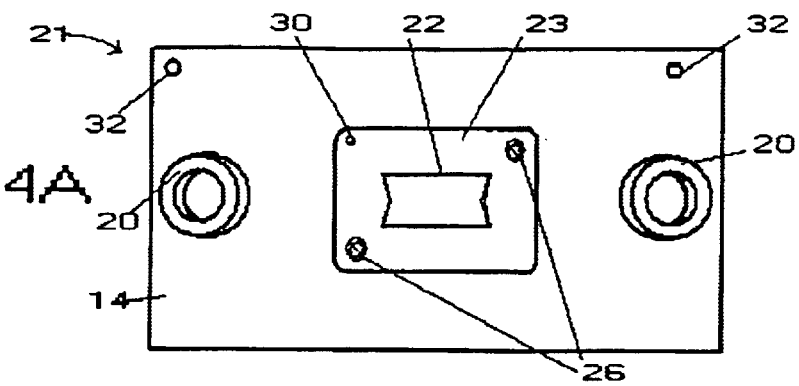
FIG. 4A is a view of the bottom side of the top portion of one of the 9-mm die set pair, showing the identifying locations of the blade's locating pins and alignment hole pattern that matches the top portion and bottom portion of the 9-mm die pair set.
Figure 4B:
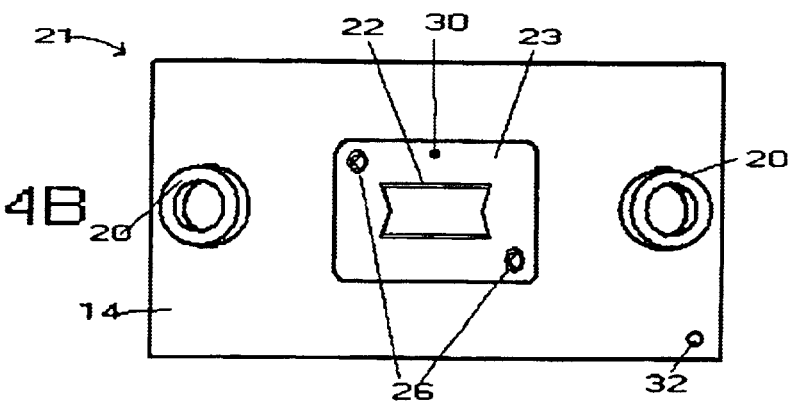
FIG. 4B is a view of the bottom side of the top portion of one of the 10-mm die set pair, showing the identifying locations of the blade's locating pins and alignment hole pattern that matches the top portion and bottom portion of the 10-mm die pair set.
Figure 4C:
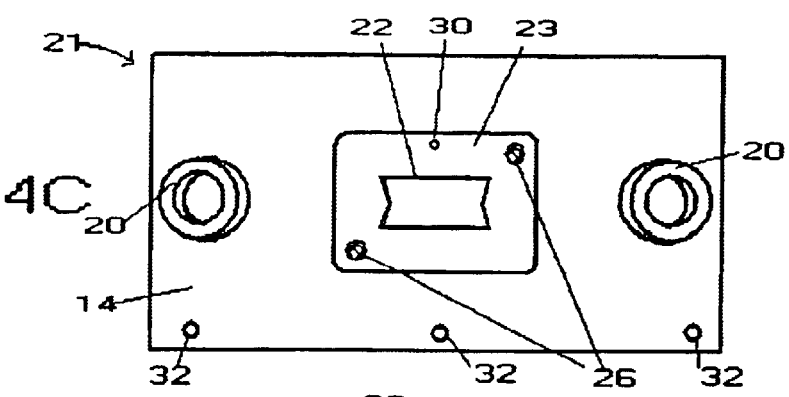
FIG. 4C is a view of the bottom side of the top portion of one of the 11-mm die set pair, showing the identifying locations of the blade's locating pins and alignment hole pattern that matches the top portion and bottom portion of the 11-mm die pair set.
Figure 4D:
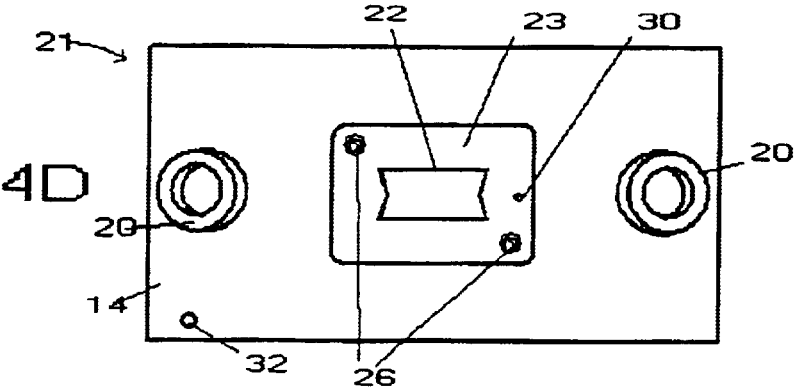
FIG. 4D is a view of the bottom side of the top portion of one of the 12-mm die set pair, showing the identifying locations of the blade's locating pins and alignment hole pattern that matches the top portion and bottom portion of the 12-mm die pair set.

FIGS. 4A, 4B, 4C and 4D show, in perspective view, the bottom sides of four preferred sizes of the upper portions 21 of matched pairs of the horizontal upper plate 21 of the present invention, along with the different locations of key holes, alignment pins and screw holes that correspond to different sizes of the dovetail width dimension T. FIG. 4A shows the upper portion 21 of the 9-millimeter cutting blade. The size of the blade the refers to the thickness T of the implant, as shown in FIG. 2C. That is, T is the internal linear dimension between the two flat, parallel faces 7 of the implant shape shown in FIG. 2C. As shown in the FIGS. 4A through 4D, each cutting blade 22 is matched in size to a specific metal plate part of a horizontal upper plate 14 by way of two features, namely the locations of the screws 26 and the location of an alignment pin 30. For example, FIG. 4A shows a 9-mm cutting blade 22 affixed to the upper portion 14 by two screws, one located in the upper right and one in the lower left in the view shown. The locator pin or alignment pin 30 is also shown for the 9-mm cutting blade to be in the upper left corner in the view shown in FIG. 4A of the main plate 14 of the upper moveable portion 21 to which the cutting blade 22 is affixed. The screws and locator pins for the cutting blades sized 10 mm, 11 mm, and 12 mm are as shown in FIGS. 4B, 4C and 4D respectively; the patterns of screws and alignment pins shown are, of course, exemplary in the sense that they show only the basic principle of matching a specific hollow cylindrical cutting blade 22 with the corresponding plate 14 to which it is intended to be attached.

In addition to the guide pins 30 for aligning the proper hollow cylindrical cutting blade 22 with the corresponding metal plate 14, allowance must also be made for matching the entire upper moveable portion 21 shown in FIGS. 4A through 4D with the corresponding stationary lower portion 16 of each die-set assembly or cutting apparatus 12. Specifically, for the 9-mm cutter shown in FIG. 4A, two "key" holes 32 are shown, one at each of the upper corners of the plate 14 as shown in the view. The key holes 32 in the upper moveable portion must match up and align with corresponding holes in the corresponding 9-mm lower stationary portion, which is not shown. That is, when the upper plate 14 holding the 9-mm blade and the 9 mm mandrel (19) are brought together so that the respective parts match, the key holes 32 of the respective upper and lower portions will align in visual vertical alignment. In FIG. 4B, a single key hole 32, at the lower right in the view, serves the same die-set matching feature of the 10-mm die cutting set. FIG. 4C shows three key holes 32 arranged across the bottom of the plate 14 in the view, so as to identify and match the two parts or portions of the 11-mm die set. FIG. 4D shows a single key hole 32 in the lower left in the view, which identifies the respective parts as a matching 12-mm dovetail set. For other shapes, i.e., not dovetail, similar alignment pins and holes would be used. The respective locating holes, or key holes, allow visual alignment of the top and bottom plates 14 and 17 respectively of the respective upper moveable portion 21 and the lower stationary portion 16 of each particular size of die-cutting set 12 as shown in FIGS. 1 and 2A.

It is not the intent of the inventors that the aforedescribed locations of key holes must be restricted to the specific locations described. Such holes can be located in alternative ways and locations and be within the spirit of the present disclosure. Alternative methods, such as notches, can also be used for identifying and aligning matched pairs of cutting parts and of the respective upper moveable portion 21 and the lower stationary portion 16 of a given cutting set 12.

Matching Pairs

To ensure precision cutting of bone implants to specific and repeatable sizes, requires the matching of mating components. The present invention contemplates the matching of three components pairs:

1. The vertically oriented mandrel 25, the hollow cylindrical cutting blade 22, and the table 24 comprise a matched cutting set.
2. The stationary base frame portion and the upper moveable portion are a matched set. They are manufactured together with the corresponding cutting parts aligned.
3. The detachable hollow cylindrical cutting blade 22 and the horizontal metal plate 14 of the upper moveable portion 21 are a matched set because they can most cost effectively be manufactured that way. Also, even though non-matched parts of similar size might operate well in relation to one another, the inventors anticipate the achieving of optimal precision cutting and system reliability if the parts that are manufactured as a set are maintained and used as a matched set.

Operation of the Invention

Referring now to FIGS. 5A and 5B, the operation of the apparatus can be described in terms of the moving actions of the two main parts, i.e., the upper moveable portion or horizontal upper plate 21 and the lower stationary portion 16 of a single die set 12. (See FIG. 2A.)

A vertebral body 50 is shown in FIG. 5A with its processes already removed. It is placed upon the table 24 (the mandrel 25 is out of view) of the lower stationary portion 16. One of two pneumatic cylinders 6 shown in FIG. 1 is actuated by way of a proximity switch box (described below but not shown in any of the FIGURES), such that the rectangular force distributing channel arch 5 that is part of the upper portion 21 has a force F exerted upon it, making it descend upon the edge of the vertebral body 50 and cutting through it until the upper portion of the die set is pressed to its deepest position, as shown in FIG. 5B when the bushings 20 make contact with the bottom plate 17. (FIG. 2A shows the mandrel in oblique view and the gap 26 between the table 24 and the mandrel 25 such that the hollow cylindrical cutting blade 22 can descend down upon and around the mandrel and its support 19.)

At the end of the downward cutting stroke, as shown in FIG. 5B, a precision cut implant 52 protrudes out of the horizonal plate 14. Residue 54 of cut bone is left on the table 24 from which it can be removed after each cut made during batch processing of vertebral bodies from a single donor.

At the end of the downward cutting stroke, the second pneumatic cylinder 6 shown in FIG. 1 lifts the moveable upper portion 21 away from the lower portion 16, and the process is repeated.

At the end of the processing of a batch of vertebral bodies from a single donor, the entire apparatus shown in FIG. 1 can be disassembled rapidly for cleaning.

Ancillary Components

The FIGS. 1 through 5B show the vertebral body cutting assembly 2 according to the present invention and the parts and moveable actions thereof. Not shown are the ancillary components that initiate and control the cutting actions.

A proximity switch box is used to trigger control box (described below) in a programmed cutting sequence in which the upper moveable portion 21 descends to drive the hollow cylindrical cutting blade 22 through the bone from which the implant is being cut. The proximity switch consists of an elongated rectangular solid having two spaced apart switches at is farthest ends from one another, i.e., spaced apart far enough to preclude single hand actuation. That is, the spaced apart arrangement of the proximity switches requires that the operator use both hands to initiate the cutting process. Two effects are achieved by this requirement of two-handed operation of the proximity switch box. First, both of the operator's hands are away the cutting assembly 2, thereby providing one safety feature. And second, the two-handed requirement of the operation of the spaced apart switches of the proximity switch box minimizes the possibility of accidental initiation of the cutting operation, as might happen if a single switch were inadvertently touched.

The proximity switch box initiates a programmed pneumatic-driven cutting sequence in a control box, placed far from the cutting assembly 2. The control box provides air to one of the pistons 6 of the two-piston assembly, forcing the upper moveable portion 21 of the die set downward upon the bone being cut.

A third and final ancillary component of the present invention is an emergency cut-off switch. The emergency cut-off switch is a rectangular solid in shape having a single red push-button switch on its top side. The operator can easily activate the emergency cut-off switch with the motion of a single hand. If the pneumatic cylinders or pistons are partially extended when the single red push-button switch is pushed, then all air is exhausted from the pneumatic cylinders. The pistons, or cylinders, and other moving parts of the invention, can then be moved freely by hand in either direction.

Resetting of the emergency switch can be done by pulling the red emergency switch button upward and by pressing an adjacent yellow reset switch button. The pneumatic cylinders will then retract to the starting position in which the upper moveable portion of the die set is farthest removed from the base plate.

We claim:

1. An apparatus for cutting shaped pieces of bone from allograft bone, the apparatus comprising:
   a. a stationary base frame comprising:
      i. a horizontal metal base plate;
      ii. a vertically oriented cylindrical mandrel supported from the base plate and having an upper flat surface;
      iii. a table surrounding the mandrel and having a top surface flush with the upper flat surface of the mandrel and having an opening therein disposed so as to create a substantially uniform gap around the uppermost flat surface of the mandrel; and
      iv. two vertical guideposts; and
   b. an upper moveable portion consisting of a horizontal metal plate with a penetration therethrough and having attached to the horizontal metal plate:
      i. two bushings that slide upon the two vertical guideposts;
      ii. a hollow cylindrical cutting blade attached to the horizontal metal plate and oriented downward from beneath the penetration; and
      iii. a force distributing channel arch spanning the penetration.

2. The apparatus of claim 1 in which the mandrel can slidably receive over it the hollow cylindrical cutting blade attached to the upper moveable portion.

3. The apparatus of claim 1 in which the mandrel and the hollow cylindrical cutting blade comprise a matched cutting set.

4. The apparatus of claim 3 in which the matched cutting set has a given cylindrical shape that is one of a series of similar shapes in different sizes each of which is defined by at least one size characterizing dimension.

5. The apparatus of claim 4 in which any object that can pass through the given cylindrical shape of the hollow cutting blade can also pass through the penetration in the horizontal metal plate part of the upper moveable portion.

6. The apparatus of claim 4 in which the given cylindrical shape of the matched cutting set consists of two opposing parallel flat faces and two opposing dihedral ends constituting a dovetail shape.

7. The apparatus of claim 6 in which the cylindrical shape consisting of two opposing parallel flat faces and two opposing dihedral ends separated by a length dimension comprise a cutting shape having a size characterizing dimension that is the width dimension between the flat parallel faces.

8. The apparatus of claim 7 in which the width dimension is variable in 1 millimeter increments and the length dimension is proportional to the size characterizing width dimension.

9. The apparatus of claim 8 in which the size characterizing width dimension is between about 8 millimeters and about 13 millimeters and most preferably of between about 9 millimeters and about 12 millimeters.

10. The apparatus of claim 4 in which the given cylindrical shape of the matched cutting set has a cross sectional shape consisting of a circle centered upon a rectangle having a characterizing length dimension that is larger than the circle and a characterizing width dimension that is smaller than the circle.

11. The apparatus of claim 10 in which the given cylindrical shape has at least one size characterizing dimension consisting of characterizing dimensions of the circle or the rectangle or both the circle and the rectangle.

12. The apparatus of claim 4 in which the given cylindrical shape of the matched cutting set is of any cross sectional shape.

13. The apparatus of claim 1 in which the stationary base frame and the upper moveable portion are a matched set.

14. The apparatus of claim 1 in which the hollow cylindrical cutting blade is contiguous with a flat mounting base flange that is detachably attached with machine screws to the horizontal metal plate of the upper moveable portion.

15. The apparatus of claim 14 in which the detachable hollow cylindrical cutting blade and the horizontal metal plate of the upper moveable portion are a matched set.

16. The apparatus of claim 15 in which the flat mounting base flange of the hollow cylindrical female cutting blade has an alignment hole that is located to engage a corresponding pin affixed to the horizontal metal plate to which the flat mounting base flange of the hollow cylindrical cutting blade detachably attaches.

17. The apparatus of claim 16 in which the alignment hole and the corresponding pin are each positioned according to the at least one size characterizing dimension of the hollow cylindrical cutting blade portion of the matched set comprised of the hollow cutting blade and the horizontal plate to which it detachably attaches.

\* \* \* \* \*